United States Patent
Tsutsumi

(10) Patent No.: US 10,450,932 B2
(45) Date of Patent: Oct. 22, 2019

(54) PARTICULATE FILTER FAULT DIAGNOSIS METHOD AND DEVICE

(71) Applicant: HINO MOTORS, LTD., Hino-shi (JP)

(72) Inventor: Munechika Tsutsumi, Tokyo (JP)

(73) Assignee: HINO MOTORS, LTD., Hino-shi (JP)

( * ) Notice: Subject to any disclaimer, the term of this patent is extended or adjusted under 35 U.S.C. 154(b) by 181 days.

(21) Appl. No.: 15/323,768

(22) PCT Filed: Jul. 1, 2015

(86) PCT No.: PCT/JP2015/068959
§ 371 (c)(1),
(2) Date: Jan. 4, 2017

(87) PCT Pub. No.: WO2016/006509
PCT Pub. Date: Jan. 14, 2016

(65) Prior Publication Data
US 2017/0159534 A1 Jun. 8, 2017

(30) Foreign Application Priority Data

Jul. 10, 2014 (JP) ................................. 2014-142177

(51) Int. Cl.
*F01N 11/00* (2006.01)
*F01N 3/021* (2006.01)
(Continued)

(52) U.S. Cl.
CPC .............. *F01N 11/00* (2013.01); *F01N 3/021* (2013.01); *F01N 3/023* (2013.01);
(Continued)

(58) Field of Classification Search
None
See application file for complete search history.

(56) References Cited

U.S. PATENT DOCUMENTS

2012/0144813 A1* 6/2012 Yahata ................. F01N 11/007
60/311
2013/0036805 A1 2/2013 Yoshioka
(Continued)

FOREIGN PATENT DOCUMENTS

EP 2 565 405 A1 3/2013
JP 2010-275977 A 12/2010
(Continued)

OTHER PUBLICATIONS

Extended European Search Report issued Jan. 3, 2018 in corresponding European Patent Application No. 15818674.2, 8 pages.
(Continued)

*Primary Examiner* — Paul M. West
*Assistant Examiner* — Mark A Shabman
(74) *Attorney, Agent, or Firm* — Oblon, McClelland, Maier & Neustadt, L.L.P.

(57) ABSTRACT

Arranged downstream of a particulate matter filter incorporated in an exhaust pipe is a PM sensor with a detection portion on which particulate matter is deposited to output a deposition amount of the particulate matter. An assumption condition is set for making an assumption that the particulate matter filter is in a reference condition having a predetermined particulate matter capturing capability. Under the assumption condition, a virtual output value is calculated depending on a virtual deposition amount of the particulate matter in the PM sensor. The particulate matter filter is determined to have fault when, upon reaching of the virtual output value to a predetermined determination threshold, an output of the PM sensor is not less than the determination threshold.

4 Claims, 7 Drawing Sheets

(51) Int. Cl.
  *F01N 3/023* (2006.01)
  *G01M 15/10* (2006.01)
  *G01N 15/08* (2006.01)

(52) U.S. Cl.
  CPC .......... *G01M 15/102* (2013.01); *G01N 15/08* (2013.01); *F01N 2550/04* (2013.01); *F01N 2560/05* (2013.01); *G01N 2015/084* (2013.01); *Y02T 10/47* (2013.01)

(56) References Cited

U.S. PATENT DOCUMENTS

2013/0312389 A1   11/2013  Yanakiev et al.
2014/0216020 A1    8/2014  Shibata et al.

FOREIGN PATENT DOCUMENTS

| | | |
|---|---|---|
| JP | 2012-122399 A | 6/2012 |
| JP | 2013-19389 A | 1/2013 |
| WO | WO 2013/035163 A1 | 3/2013 |

OTHER PUBLICATIONS

International Search Report dated Sep. 29, 2015, in PCT/JP2015/068959, filed Jul. 1, 2015.

\* cited by examiner

PARTICULATE FILTER FAULT DIAGNOSIS METHOD AND DEVICE

TECHNICAL FIELD

The present invention relates to a method and a device for making fault diagnosis of a particulate matter filter to precisely and favorably determine abnormality in the particulate matter filter.

BACKGROUND ART

Particulate matter (PM) discharged from a diesel engine is mainly constituted by carbonic soot and a soluble organic fraction (SOF) of high-boiling hydrocarbon and contains a trace of sulfate (misty sulfuric acid fraction). In order to reduce such particulate matter, conventionally a particulate matter filter has been incorporated in an exhaust pipe through which exhaust gas flows.

Such particulate matter filter has a porous honeycomb structure made of ceramics such as cordierite and having lattice-like compartmentalized passages. Alternate ones of the passages have plugged inlets and the remaining passages with unplugged inlets have plugged outlets. Discharged downstream is only the exhaust gas passing through thin porous walls which compartmentalize the passages.

The particulate matter in the exhaust gas, which is captured and deposited on inner surfaces of the thin porous walls, requires to be forcedly heated and burned off so as to regenerate the particulate matter filter.

Specifically, it has been conducted to arrange, in front of the particulate matter filter, a flow-through type oxidation catalyst upstream of which fuel is added so that the added fuel undergoes oxidization reaction through the oxidation catalyst and the exhaust gas elevated in temperature by resultant reaction heat is guided to the particulate matter filter to increase a catalyst bed temperature to thereby burn off particulate matter, resulting in regeneration of the particulate matter filter. As a measure for executing the fuel addition, main injection of the fuel near a compression upper dead center may be followed by post injection of the fuel at non-ignition timing after the compression upper dead center to thereby add the fuel to the exhaust gas.

This kind of particulate matter filter may have fault due to, for example, erosion of the filter through combustion of much particulate matter all at once or breakage of the filter through mechanical shock or the like. When driving is continued with the particulate matter filter having the fault, the particulate matter discharged from an engine cannot be properly removed from exhaust gas, resulting in discharge of the particulate matter as atmospheric contaminant into atmosphere.

Thus, it has been conducted to mount on a vehicle an OBD (on-board diagnostics) system which automatically determines fault of a particulate matter filter through self-diagnosis so that a driver is informed of the fault in and is urged to replace the particulate matter filter. The fault of the particulate matter filter may be determined, for example, through detection of pressures of the exhaust gas upstream and downstream of the particulate matter filter; the particulate matter filter is diagnosed as having fault when difference between the detected pressures is lower than a predetermined value.

Regulations on exhaust gas from a vehicle tend to be strengthened year by year. Especially in U.S.A., there is circumstance that installation of an OBD system for fault determination of an exhaust emission control device in a vehicle has been obliged ahead of other countries and there is a prospect in near future that the regulations on fault determination of an exhaust emission control device will be further strengthened. The above-mentioned determination through the detection of the pressures will be insufficient to cope with such severe regulations. Thus, a method has been demanded which can determine fault of a particulate matter filter more precisely than ever before.

As a device capable of determining fault of a particulate matter filter with a higher degree of precision, there has been proposed, for example, a so-called deposition-type particulate matter sensor (PM sensor) in which particulate matter is deposited on a surface of a foundation with two electrodes, voltage being applied between the electrodes to output an electric current depending on an deposition amount of the particulate matter. With such PM sensor provided downstream of the particulate matter filter, fault of the particulate matter filter can be determined on the basis of the deposition amount or a deposition velocity of the particulate matter on the PM sensor. There exists, for example, below-mentioned Patent Literature 1 pertinent to this kind of device for making fault diagnosis of a particulate matter filter. Disclosed in Patent Literature 1 is a PM sensor arranged downstream of a particulate matter filter. Assuming that the particulate matter filter is in a predetermined state, a cumulative amount of the particulate matter having passed through the particulate matter filter during a predetermined period is estimated on the basis of, for example, a driving state of an engine while the cumulative amount of the particulate matter having passed through the particulate matter filter during the predetermined period is calculated on the basis of an output value of the PM sensor. Whether the particulate matter filter has fault or not is diagnosed by comparing the calculated and estimated cumulative amounts of the particulate matter.

CITATION LIST

Patent Literature

Patent Literature 1: JP 2013-019389A

SUMMARY OF INVENTION

Technical Problems

However, a concentration of particulate matter in the exhaust gas may vary depending on various conditions such as not only a rotation frequency of the engine but also a fuel injection amount and a temperature of the exhaust gas; the deposition velocity of the particulate matter in the PM sensor may vary depending on a flow rate of the exhaust gas. Thus, estimation of the discharged amount or deposition velocity of the particulate matter from, for example, the driving state of the engine is limitative in precision. Especially, when the driving state of the engine drastically varies during the predetermined period, a difference between actual and estimated discharge amounts of the particulate matter may become greater, resulting in increased concern of erroneous diagnosis on fault of the particulate matter filter.

Therefore, in the above-mentioned Patent Literature 1, when the difference between the actually discharged amount of the particulate matter from the engine and a reference discharge amount of the particulate matter depending on the driving state of the engine becomes greater than a predetermined amount, the amount or timing of fuel injection is controlled to increase/decrease the actually discharged amount of the particulate matter from the engine so as to enhance precision of fault diagnosis of the particulate matter filter. However, even doing so, depending on setting of the predetermined value as threshold for increase/decrease control of the particulate matter, precision of fault diagnosis of the particulate matter filter is not always enhanced; rather it is deemed that such artificial control may increase the error. In Patent Literature 1, there may be the case where the discharged amount of the particulate matter is increased so as to keep precision of fault diagnosis, which may bring about deteriorated fuel efficiency due to superfluous fuel consumption and/or increase in discharged amount of the particulate matter into atmosphere.

The invention was made in view of the above and has its object to provide a method and a device for making fault diagnosis of a particulate matter filter which can precisely and favorably determine fault of the particulate matter filter.

Solution to Problems

The invention is directed to a method for making fault diagnosis of a particulate matter filter, which comprises arranging a PM sensor downstream of the particulate matter filter incorporated in an exhaust pipe, said PM sensor having a detection portion on which particulate matter is deposited to output a deposition amount of said particulate matter, setting an assumption condition for making assumption that said particulate matter filter is in a reference state having a predetermined particulate matter capturing capability, calculating a virtual output value in said PM sensor depending on a virtual deposition amount of the particulate matter under said assumption condition, and determining said particulate matter filter to have fault when, upon reaching of said virtual output value to a predetermined determination threshold, an output of said PM sensor is not less than said determination threshold.

Thus, by comparing the virtual output value of the PM sensor estimated from, for example, the driving state with the actual output value of the PM sensor in this manner, fault of the particulate matter filter can be favorably determined.

It is preferable in the method for making fault diagnosis of the particulate matter filter according to the invention that said determination threshold is a saturation output value of said PM sensor. Then, fault determination of the particulate matter filter can be executed at a proper timing.

It is preferable in the method for making fault diagnosis of the particulate matter filter according to the invention that the fault diagnosis is executed by employing only the output value in a case where said PM sensor is in a state capable of outputting the output value depending on the deposition amount of the particulate matter. Then, the precision of the fault diagnosis of the particulate matter filter can be further enhanced.

The invention is also directed to a device for making fault diagnosis of a particulate matter filter comprising the particulate matter filter incorporated in an exhaust pipe, a PM sensor arranged downstream of said particulate matter filter and having a detection portion on which particulate matter is deposited to detect the particulate matter in exhaust gas, and a controller with an assumption condition being set for making assumption that said particulate matter filter is in a reference state having a predetermined particulate matter capturing capability, wherein said controller calculates under said assumption condition a virtual output value in said PM sensor depending on a virtual deposition amount of the particulate matter and determines said particulate matter filter to have fault when, upon reaching of said virtual output value to a predetermined determination threshold, an output of said PM sensor is not less than said determination threshold.

It is preferable in the device for making fault diagnosis of the particulate matter filter according to the invention that a saturation output value of said PM sensor is adapted to be used as said determination threshold.

It is preferable in the device for making fault diagnosis of the particulate matter filter according to the invention that said fault diagnosis is adapted to be executed by employing only the output value in a case where said PM sensor is in a state capable of outputting the output value depending on the deposition amount of the particulate matter.

Advantageous Effects of Invention

A method and a device for making fault diagnosis of a particulate matter filter according to the invention can have an excellent effect that fault in the particulate matter filter can be determined precisely and favorably.

DESCRIPTION OF EMBODIMENT

An embodiment of the invention will be described in conjunction with attached drawings.

Figure 1:
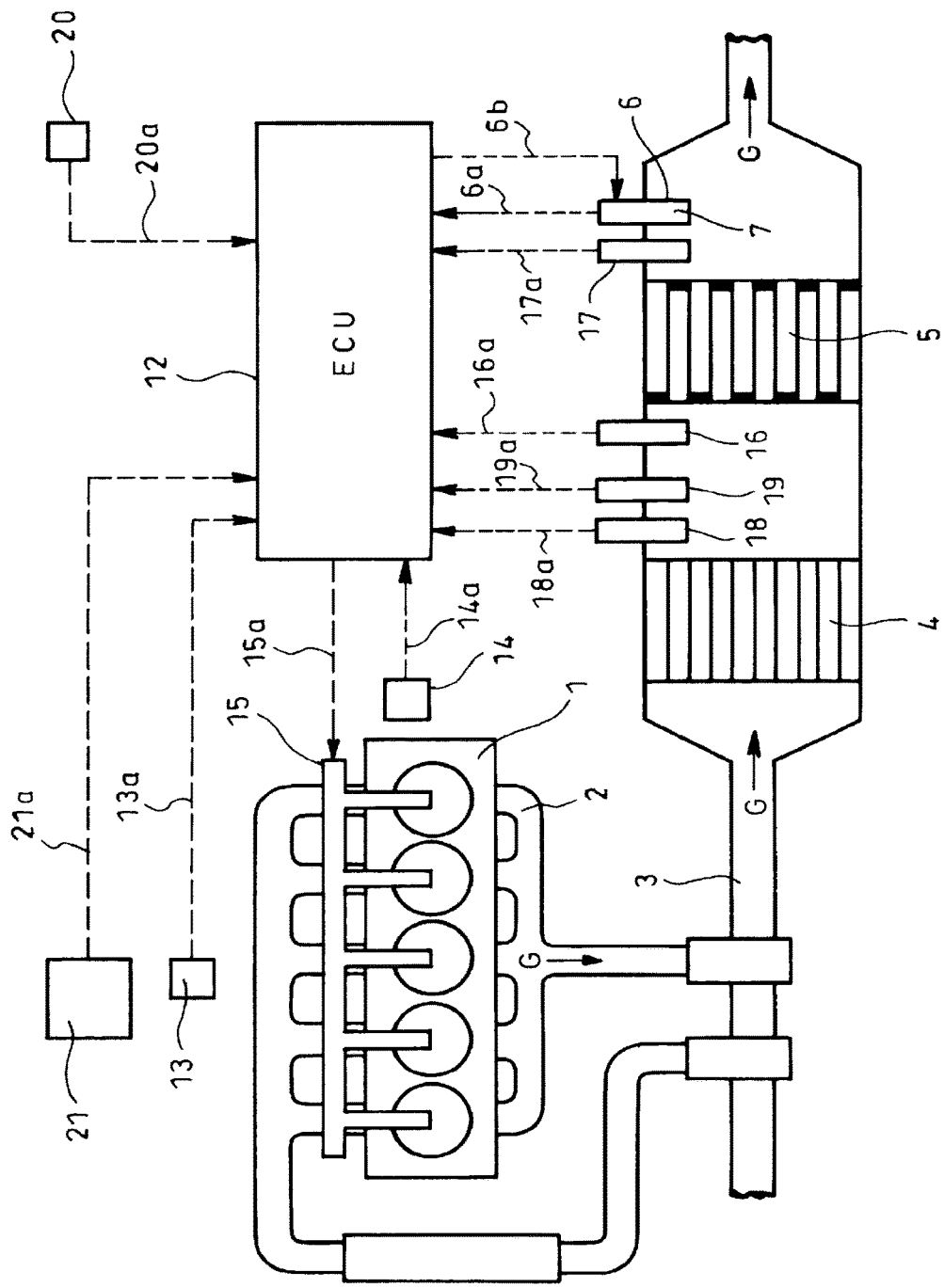
FIG. 1 is a schematic diagram showing an embodiment of the invention.

FIG. 1 shows an embodiment of a method and a device for making fault diagnosis of a particulate matter filter according to the invention. Incorporated in an exhaust pipe 3, through which flows exhaust gas G from an engine 1 through an exhaust manifold 2, is a catalyst-regenerative particulate matter filter 5 with an oxidation catalyst 4 being arranged in front thereof. Arranged downstream of the particulate matter filter 5 is a PM sensor 6.

Figure 2:
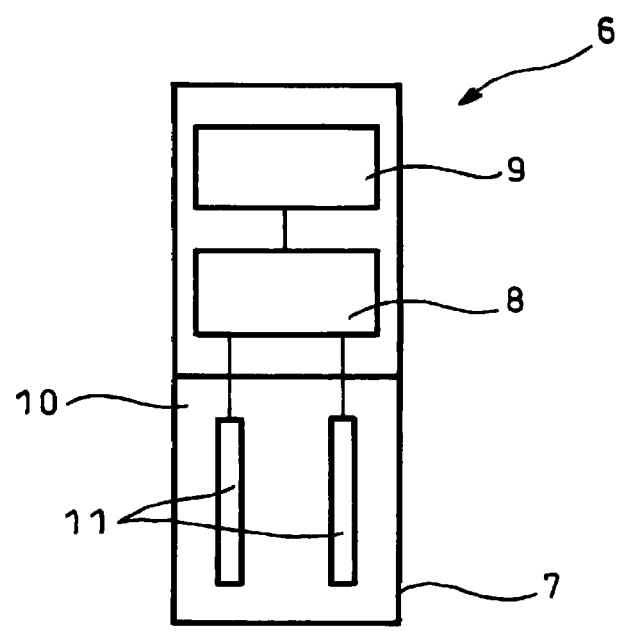
FIG. 2 is a schematic diagram showing a configuration of a PM sensor in the embodiment of the invention.

The PM sensor 6 comprises, as shown in FIG. 2, a detection portion 7 on which particulate matter is deposited for detection, an output portion 8 for application of voltage to and for output of electric current from the detection portion 7 and a control portion 9 for control of the output portion 8. The detection portion 7 has a foundation 10 on a surface of which two electrodes 11 are arranged. The foundation 10 is a ceramic insulator and the electrodes 11 are arranged on the foundation 10 in a spaced-apart relationship from each other so that the electrodes 11 are isolated each other. As shown in FIG. 1, the PM sensor 6 is incorporated in the exhaust pipe 3 in a manner inserted from outside and downstream of the particulate matter filter 5 in front of which in turn the oxidation catalyst 4 is arranged. In this connection, the PM sensor 6 is arranged such that the detection portion 7 is projected inside of the exhaust pipe 3 and the surface with the electrodes 11 of the detection portion 7 is directed upstream. Applied to between the electrodes 11 on the detection portion 7 is a predetermined voltage from the output portion 8.

Figure 3:
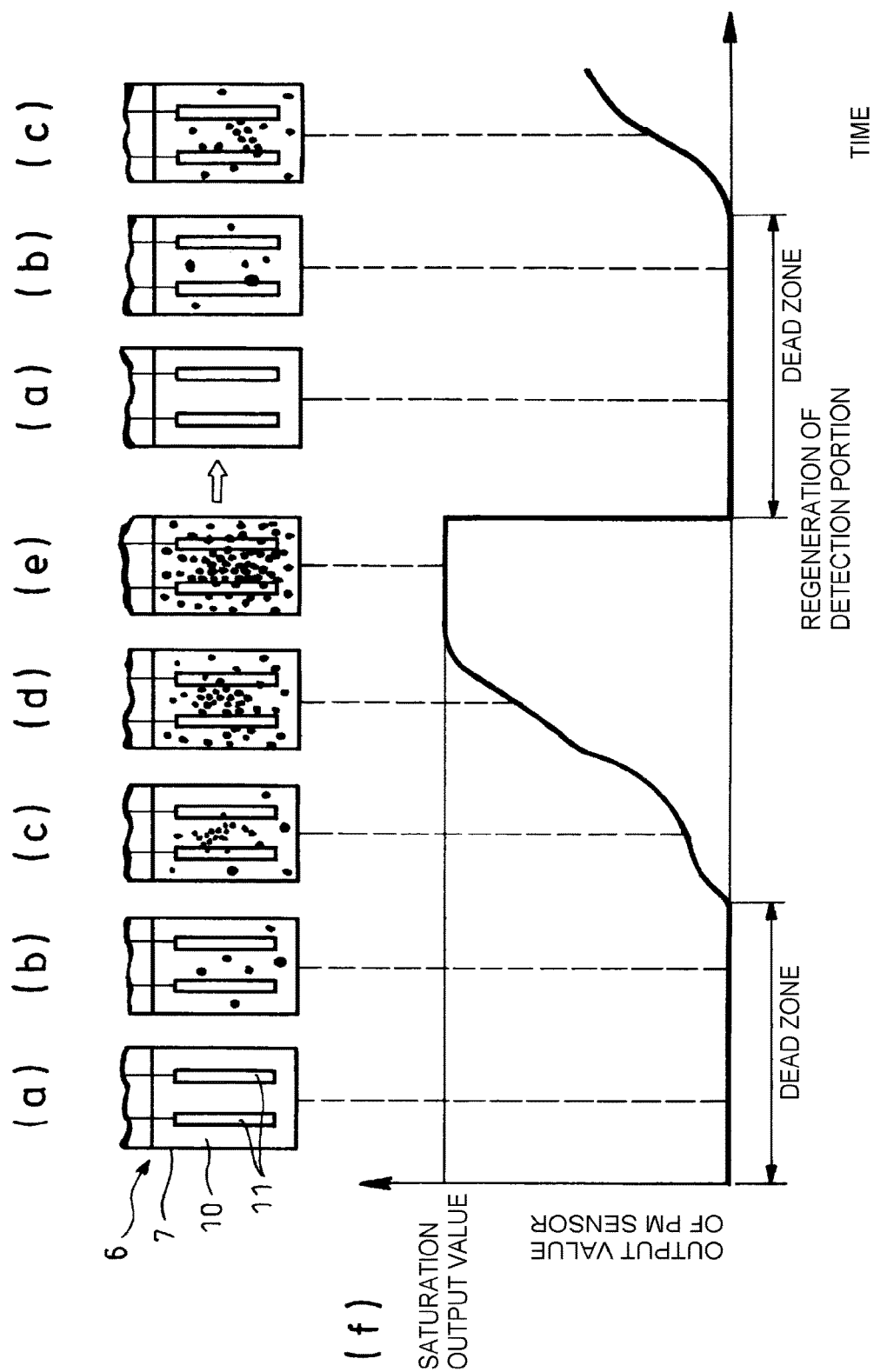
FIG. 3 is a concept diagram showing an operation of the PM sensor in the embodiment of the invention.

An operation of the PM sensor 6 in such device will be described. Most of the particulate matter produced through the driving of the engine 1 is captured by the particulate matter filter 5, and the particulate matter not captured passes through the filter 5 and is partly deposited on the detection portion 7 of the PM sensor 6 downstream. In FIG. 3, (a)-(e) schematically show that the particulate matter in the exhaust gas G having passed through the particulate matter filter 5 is gradually deposited on the surface of the detection portion 7 of the PM sensor 6; and (f) schematically shows variation in output of the PM sensor 6 depending on variation in deposition amount of the particulate matter.

In a state with no deposition of the particulate matter ((a) in FIG. 3), the electrodes 11 of the detection portion 7 are isolated as mentioned in the above so that, even if the voltage is applied to between the electrodes 11, no flow of electric current occurs between the electrodes 11. Even if the particulate matter begins to be deposited on the surface of the detection portion 7 into a state where a slight amount of particulate matter is deposited as shown in (b) of FIG. 3, no flowing of electric current occurs between the electrodes 11. Such a period in which an output value of the PM sensor is zero because of the deposition amount of the particulate matter being zero or little is called a dead zone.

When the particulate matter has the deposition amount exceeding a certain amount to bridge the electrodes 11 as shown in (c) in FIG. 3, electric current begins to flow between the electrodes 11 through the particulate matter and is outputted from the output portion 8 since the particulate matter containing carbon as a major component is conductive material. That is, the PM sensor 6 outputs, as electric current, the deposition amount of the particulate matter on the surface of the detection portion 7.

As the particulate matter is further increased in deposition amount ((d) in FIG. 3), a value of electric resistance between the electrodes 11 lowers so that the output value from the detection portion 7 increases. When the deposition amount of the particulate matter reaches a certain value or more ((e) in FIG. 3), a flowing current amount between the electrodes 11 saturates and the output of the detection portion 7 does not increase any more.

After the output reaches the saturation output value, the control portion 9 of the PM sensor 6 is controlled to regenerate the detection portion 7 at a predetermined timing. Specifically, the control portion 9 receives a regeneration signal from outside to transmit a command for heating of the detection portion 7 to the output portion 8. The output portion 8 executes an operation of heating the detection portion 7 to burn off the deposited particulate matter on the detection portion V. The operation of heating the detection portion 7 is executed, for example, such that higher voltage is applied between the electrodes 11 to make the electric current flowing through the deposited particulate matter to generate Joule heat. The particulate matter is burned off to regenerate and return the detection portion 7 into the state of (a) in FIG. 3; when deposited again into the state of (e) in FIG. 3, the particulate matter is burned off again at the predetermined timing to return the detection portion 7 into the state of (a) in FIG. 3.

Thus, the output value of the PM sensor 6 is varied as shown in (f) in FIG. 3 in accordance with particulate-matter-deposition/regeneration cycle in the detection portion 7. The output value is momentarily inputted as output electric current 6a to a controller 12 which constitutes an engine control computer (ECU: electronic control unit) (see FIG. 1). The controller 12 serves also to input a regeneration signal 6b to the control portion 9 of the PM sensor 6 at the predetermined timing in the above-mentioned cycle of the PM sensor 6 to thereby regenerate the PM sensor 6.

The controller 12, which serves also as the engine control computer, has also a role of controlling fuel injection. Specifically, on the basis of an accelerator opening degree signal 13a from an accelerator sensor 13 which detects an accelerator opening degree as load of the engine 1 as well as a rotation frequency signal 14a from a rotation sensor 14 which detects a rotation frequency of the engine 1, a fuel injection signal 15a is outputted to a fuel injection unit 15 which injects fuel to the respective cylinders of the engine 1.

The fuel injection unit 15 comprises a plurality of injectors each for each cylinder, and electromagnetic valves each for each injector are properly valve-opening controlled by the fuel injection signal 15a to properly control a fuel injection timing (valve-opening timing) and a fuel injection amount (valve-opening time).

In the controller 12, the fuel injection signal 15a in a normal mode is decided on the basis of the accelerator opening degree and the engine rotation frequency as mentioned in the above while, when the forced regeneration of the particulate matter filter 5 is to be executed, the normal mode is changed into a regeneration mode where decided is the fuel injection signal 15a with an injection pattern such that main injection of the fuel near the compression upper dead center is followed by post injection at non-ignition timing after the compression upper dead center.

Thus, in the embodiment, the fuel injection unit 15 serves also as fuel addition means for the forced regeneration of the particulate matter filter 5. Specifically, as mentioned in the above, the main injection is followed by the post injection at non-ignition timing after the compression upper dead center; such post injection brings about addition of unburned fuel into the exhaust gas G. The unburned fuel makes oxidation reaction on the oxidation catalyst 4 in front of the particulate matter filter 5; resultant reaction heat increases a catalyst bed temperature to burn off the particulate matter captured by the particulate matter filter 5.

Upon executing such forced regeneration of the particulate matter filter 5, for example, difference of pressures upstream and downstream of the particulate matter filter 5 is calculated on the basis of pressure signals 16a and 17a from pressure sensors 16 and 17 arranged upstream and downstream of the particulate matter filter 5, respectively. On the basis of the pressure difference calculated, the deposition amount of particulate matter in the particulate matter filter 5 is estimated and timing for the forced regeneration is decided on the basis of the estimated deposition amount.

There are various ways for estimating such deposition amount of the particulate matter. For example, a basic production amount of the particulate matter may be estimated on the basis of a current driving state of the engine 1, and may be multiplied by a correction factor in consideration of various parameters concerned with the production of the particulate matter and then a treated amount of the particulate matter in the current driving state of the engine may be subtracted therefrom to obtain a final production amount of the particulate matter. Such final production amount may be momentarily cumulated to estimate the deposition amount of the particulate matter in the particulate matter filter 5.

In addition, monitored in the controller 12 are various values such as a temperature signal 18a of the exhaust gas G from a temperature sensor 18 arranged upstream of the particulate matter filter 5, a flow rate signal 19*a* of the exhaust gas G from a flow rate sensor 19 arranged upstream of the particulate matter filter 5 and an atmospheric signal 20*a* from an atmospheric sensor 20 which measures environmental atmospheric pressure. Executed on the basis of such values are various controls on the driving of the vehicle.

An instrument panel in a cab is provided with an alarm lamp 21 which announces fault in the particulate matter filter 5 to the driver.

Fault determination of the particulate matter filter 5 in the above-mentioned device will be described. As mentioned in the above, the output current 6*a* from the PM sensor 6 is momentarily inputted to the controller 12. Concurrently, set in the controller 12 is an assumption condition for making an assumption that the particulate matter filter 5 is in a reference state having a predetermined particulate matter capturing capability. A virtual output value of the PM sensor 6 is calculated under such assumption condition, on the basis of statistical model and from values such as the rotation frequency signal 14*a* inputted from the rotation sensor 14 for the engine 1, the fuel injection amount decided in the controller 12, the temperature signal 18*a* of the exhaust gas G inputted from the temperature sensor 18, the flow rate signal 19*a* of the exhaust gas G inputted from the flow rate sensor 19 and the atmospheric signal 20*a* inputted from the atmospheric sensor 20. Specifically, when the particulate matter filter 5 is assumed to be in the reference state having the predetermined particulate matter capturing capability, the deposition amount of the particulate matter in the PM sensor 6 downstream thereof can be estimated as the virtual deposition amount by calculation and cumulation as function of the rotation frequency of the engine 1, the injection amount of the fuel, the temperature and flow rate of the exhaust gas G, the atmospheric pressure and the like; and the virtual output value of the PM sensor 6 is determined depending on such virtual deposition amount. Thus, the virtual output value of the PM sensor 6 can be calculated on the basis of the statistical model and as function of the rotation frequency of the engine 1, the injection amount of the fuel, the temperature and flow rate of the exhaust gas G, the atmospheric pressure and the like. And, at the predetermined timing, the virtual output value is compared with the actual output value of the output current 6*a* in the PM sensor 6 to make fault determination of the particulate matter filter 5.

Figure 4:
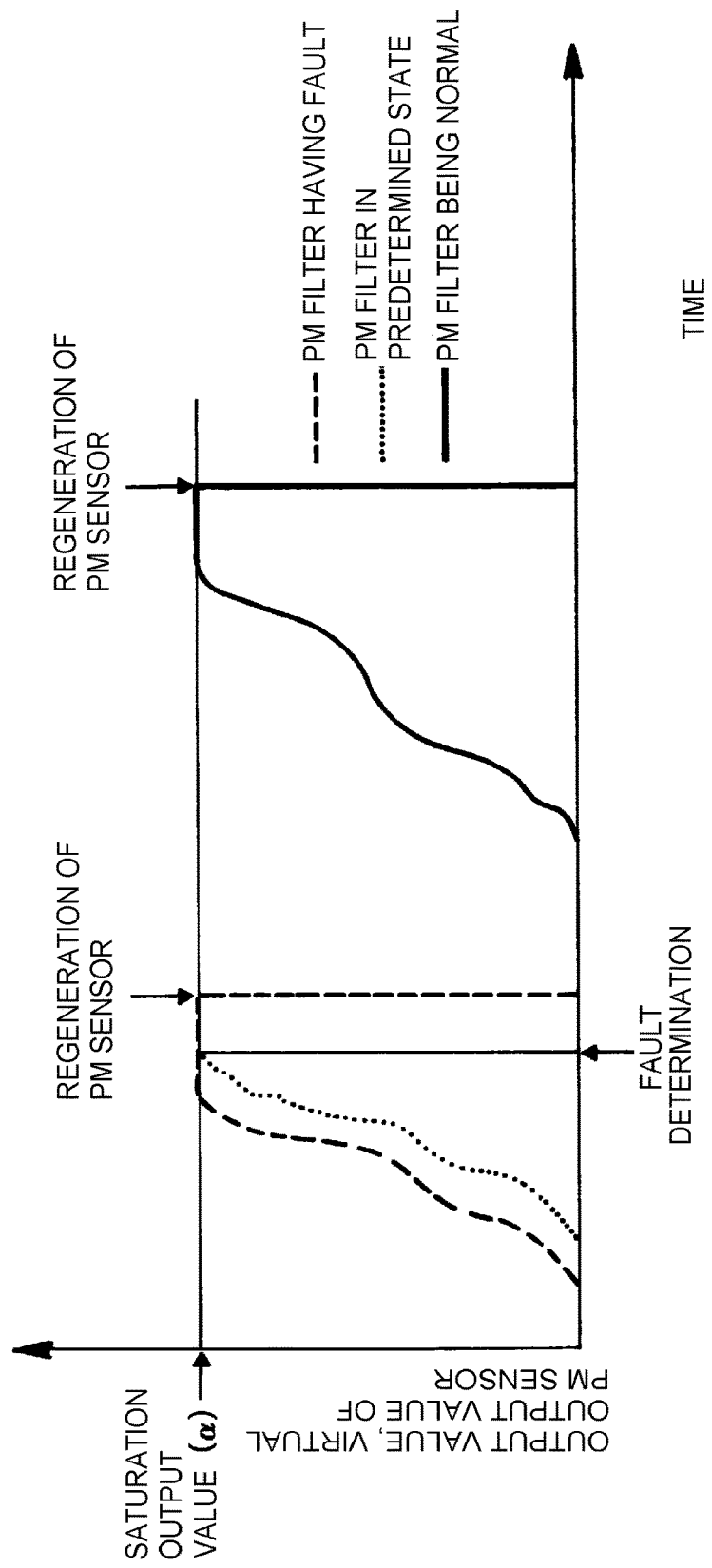
FIG. 4 is a concept diagram showing variation in output value of the PM sensor in the embodiment of the invention.

Specifically, if the particulate matter filter 5 is normal, the value of the output current 6*a* from the PM sensor 6 is in accordance with increase in deposition amount of the particulate matter with lapse of time and has a change as shown in solid line in a graph of FIG. 4 such that the dead zone is followed by the increase and then saturation of the output. By contrast, if the particulate matter filter 5 has fault, much particulate matter passes through the particulate matter filter 5, which results in fastness in deposition velocity of the particulate matter on the PM sensor 6 and shortness in time from the dead zone into saturation through increase of the output. Thus, in the controller 12 of the embodiment, the particulate matter filter 5 is assumed to be in the reference state having the predetermined particulate matter capturing capability and, under such assumption, the virtual output value of the PM sensor 6 is calculated as mentioned in the above on the basis of the various conditions. Here, "the reference state having the predetermined particulate matter capturing capability" of the particulate matter filter 5 assumed in the controller 12 refers to, for example in the embodiment, the particulate matter filter in a fault state where the particulate matter is discharged three times (0.03 g/bhph) as much as regulation standard. The invention is not limited to this value; in other embodiments, other value may be used as reference.

The virtual output value of the PM sensor 6 calculated from the estimated cumulation value of the particulate matter in the controller 12 has a change, for example, as shown in dotted line in FIG. 4. Upon reaching of the virtual output value to the predetermined determination threshold $\alpha$, fault determination of the particulate matter filter 5 is executed. Specifically, at the time point, if the value of the output current 6*a* from the PM sensor 6 has reached the determination threshold $\alpha$ (a case illustrated in broken line in FIG. 4), the particulate matter filter 5 is determined to have fault; if the value of the output current 6*a* does not reach the determination threshold $\alpha$ (the case illustrated in solid line in FIG. 4), the particulate matter filter 5 is determined to have an enough particulate matter capturing capability and be normal.

Thus, in this manner, the virtual output value of the PM sensor 6 estimated from the driving state and the like can be compared with the actual value of the output current 6*a* from the PM sensor 6 to properly determine fault of the particulate matter filter 5.

In the device as disclosed in above-mentioned Patent Literature 1, the cumulative amount of the particulate matter passing through the particulate matter filter in a case where the particulate matter filter is assumed to be in a predetermined state is estimated while the cumulative amount of the particulate matter passing through the particulate matter filter is calculated on the basis of the output value of the PM sensor, both of the estimated and calculated values being compared with each other. Thus, there is a fair possibility of causing error since both the values compared include calculation processes. By contrast, in the embodiment, one of the compared values is the actually measured value so that there is little room of causing error.

Moreover, in the embodiment, unlike the device disclosed in Patent Literature 1, there is no superfluous fuel consumption upon fault diagnosis of the particulate matter filter 5.

As the above-mentioned determination threshold $\alpha$, the saturation output value of the PM sensor 6 may be used; fault determination may be executed at a timing when the virtual output value reaches the saturation output value. Because, fault determination of the particulate matter filter 5 executed with smaller determination threshold $\alpha$, i.e., with shorter time up to the determination would increase an influence of any error or malfunction; on the other hand, any determination threshold $\alpha$ greater than the saturation output value would be nonsense since fundamentally the output value of the PM sensor 6 does not become greater than the saturation output value. Use of the saturation output value as the determination threshold $\alpha$ enables execution of fault determination on the particulate matter filter 5 at proper timing.

In this connection, the fault diagnosis of the particulate matter filter 5 may be conducted by repeating the above-mentioned determination for a plurality of times and diagnosing the particulate matter filter 5 as having fault when a number of times determined to have fault out of a total number of the determinations executed is not less than a certain threshold, which can minimize a possibility that occurrence of temporal erroneous determination due to some unexpected cause such as malfunction of any machine results in erroneous diagnosis.

When the particulate matter filter 5 is diagnosed as having fault, a fault announcement signal 21*a* is inputted to an alarm lamp 21 to switch on the lamp 21, which urges the driver to replace the particulate matter filter 5.

Figure 5:
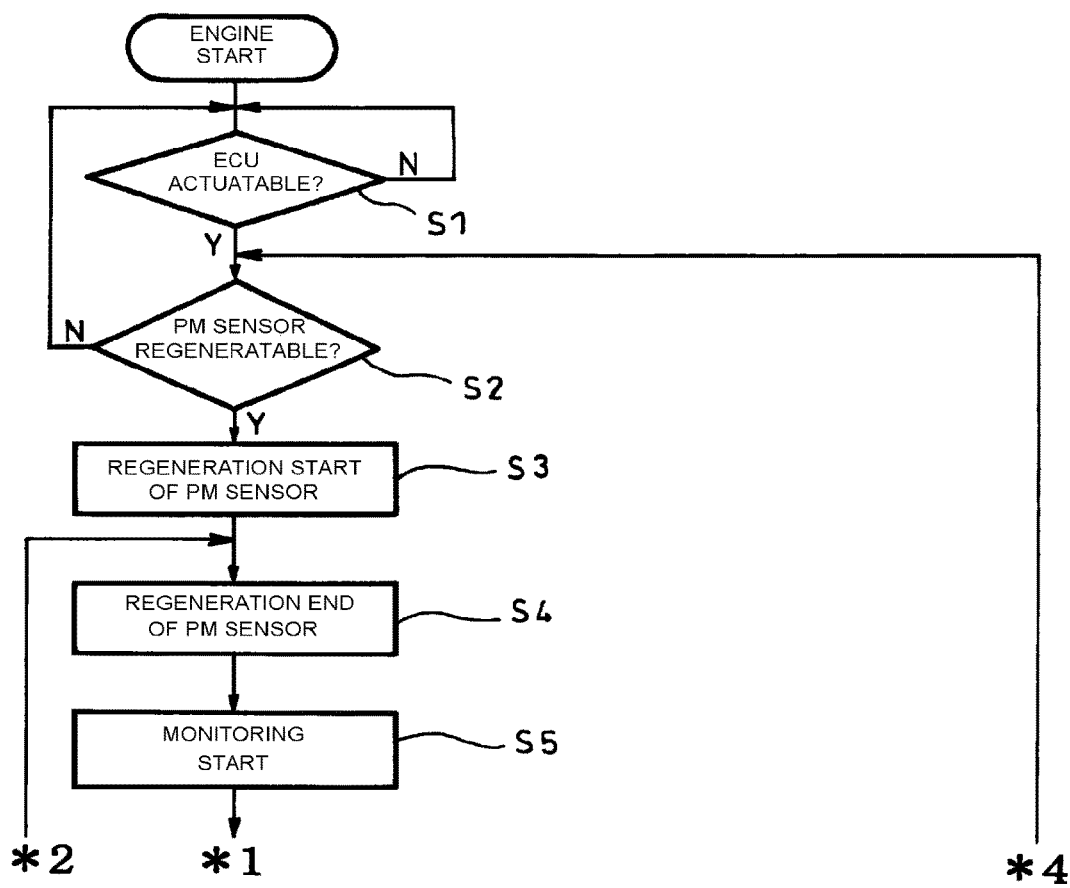
FIGS. 5, 6 and 7 are a flow chart showing steps for diagnosis of a particulate matter filter in the embodiment of the invention.
Figure 6:
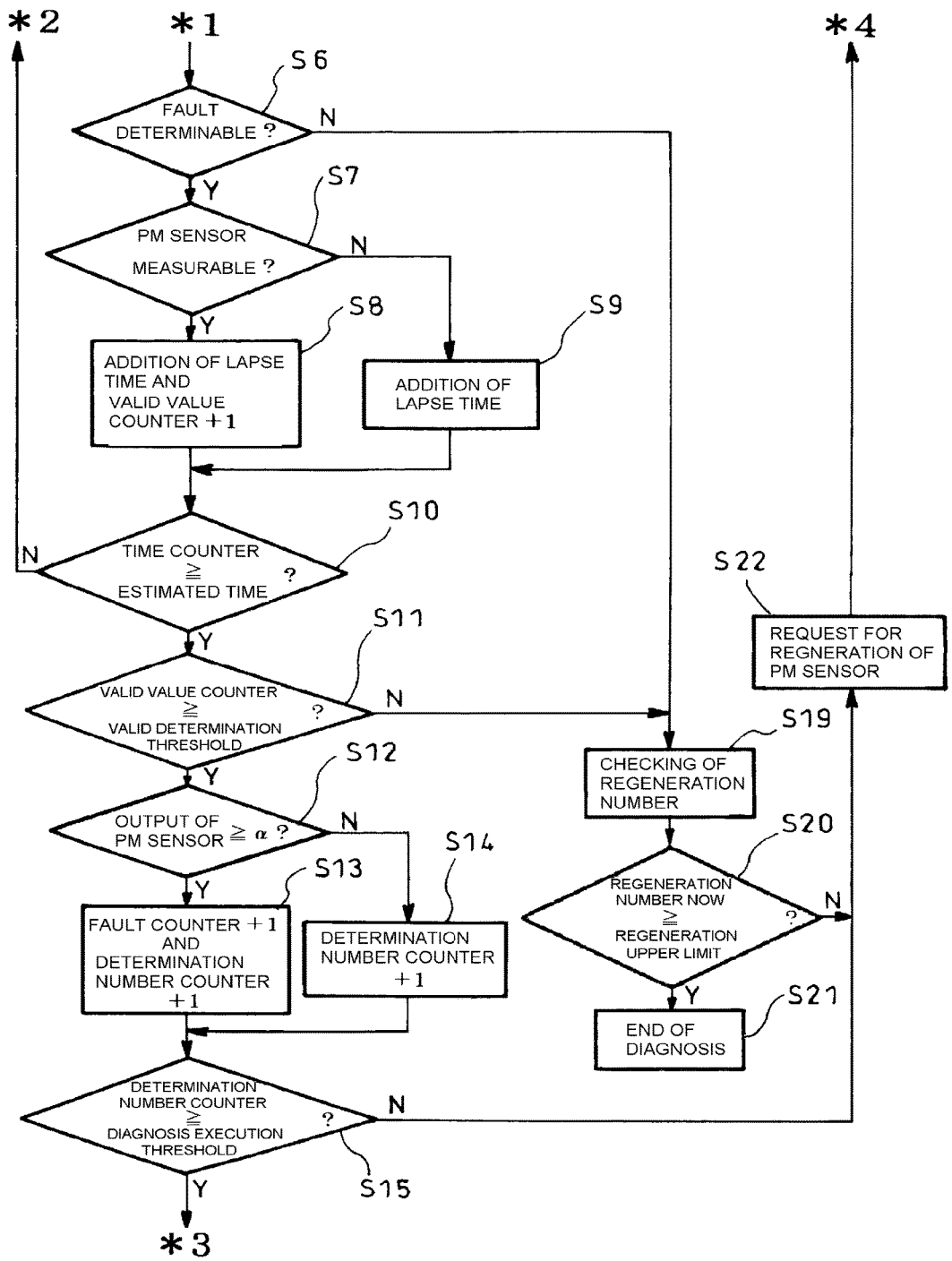
Figure 7:
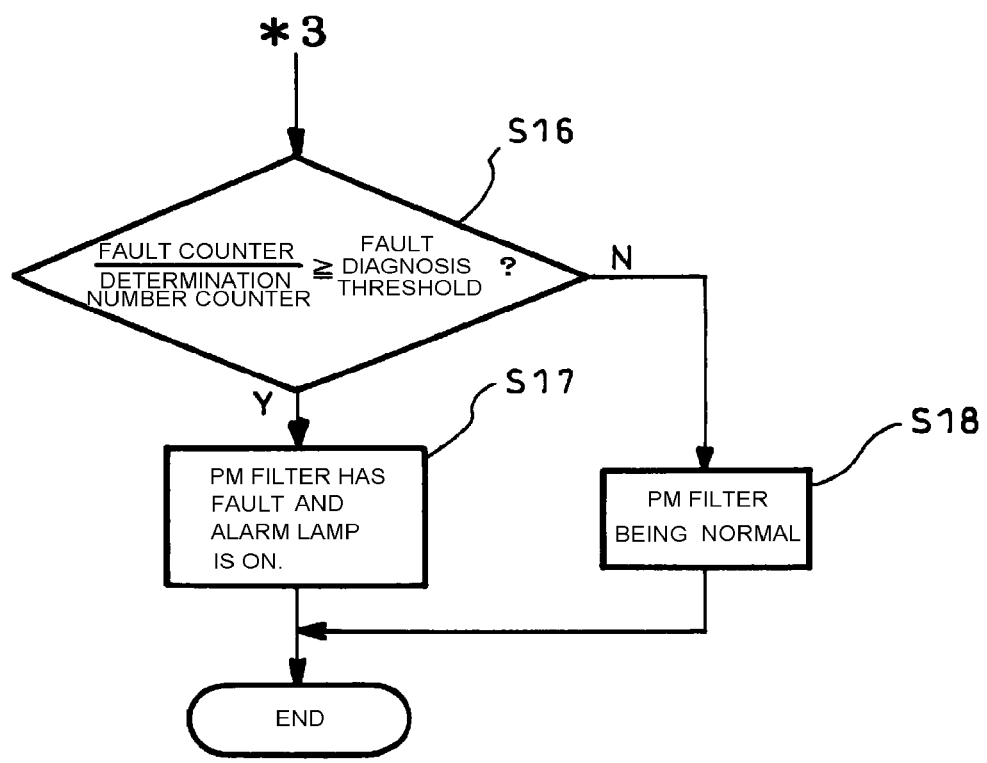

Next, a specific procedure of the fault diagnosis of the particulate matter filter 5 in the above-mentioned embodiment will be described in conjunction with FIGS. 5-7 which totally show one flow; *1 in FIG. 5 and *2, *3 and *4 in FIG. 6 are respectively in connection with *1 in FIG. 6, *2 in FIG. 5, *3 in FIG. 7 and *4 in FIG. 5.

After the engine 1 is started to start the driving, primarily executed is regeneration of the PM sensor 6 to reset the deposition state of the particulate matter; prior to that, executed in steps S1-S2 is to determinate whether the device is in a state capable of executing the regeneration of the PM sensor 6 (FIG. 5) or not. Executed in step S1 is checking of the controller 12; and in step S2, checking of the PM sensor 6. Specifically, for example, whether temperatures of the controller 12 and PM sensor 6 are over a dew point or not is checked by temperature sensors or the like (not shown) since the operation of the controller 12 bedewed and the regeneration of the PM sensor 6 bedewed may break the controller 12 and the PM sensor 6, respectively. Here, if the device is determined not to be in the state capable of regenerating the PM sensor 6 ("N" in step S1 or S2), the procedure returns to step S1 and steps S1-S2 are repeated until the regeneration of the PM sensor 6 becomes possible.

If the regeneration of the PM sensor 6 is determined to be possible in steps S1-S2 ("Y" in steps S1 and S2), the procedure goes to step S3 where the regeneration of the PM sensor 6 is executed. Specifically, the regeneration signal 6b is inputted from the controller 12 to the control portion 9 of the PM sensor 6 (see FIG. 1). The control portion 9 having received the regeneration signal 6b executes control on the output portion 8 to apply higher voltage to between the electrodes 11 so that resultant Joule heat burns off the particulate matter deposited on the surface of the foundation 10.

When the regeneration of the PM sensor 6 is ended (step S4), started as step S5 is monitoring for fault determination of the particulate matter filter 5. Specifically, the virtual output value from the PM sensor 6 is calculated from statistical model, under the assumption that the particulate matter filter 5 is in the reference state having the predetermined particulate matter capturing capability and as a function of the values such as the rotation frequency signal 14a inputted from the rotation sensor 14 for the engine 1, the fuel injection amount determined in the controller 12, the temperature signal 18a of the exhaust gas G inputted from the temperature sensor 18, the flow rate signal 19a of the exhaust gas G inputted from the flow rate sensor 19 and the atmospheric signal 20a inputted from the atmospheric sensor 20; the calculated virtual output value is cumulated momentarily.

Next, executed in steps S6-S11 are confirmation of a state of the PM sensor 6 and sifting of output data on the basis of the state of the PM sensor 6 (FIG. 6) prior to fault determination of the particulate matter filter 5. Specifically, depending on the state of the PM sensor 6 and/or its environment, there may be a fear that the PM sensor 6 is broken and/or the deposition amount of particulate matter cannot be properly and precisely measured by the PM sensor 6; fault determination of the particulate matter filter 5 executed by the PM sensor 6 with lowered precision may bring about erroneous determination. Thus, in steps S6-S11, whether the PM sensor 6 is in a state suitable for fault diagnosis of the particulate matter filter 5 or not is checked on the basis of the temperature of the exhaust gas G and the like; in a case where determined not to be in the state suitable for diagnosis of the particulate matter filter 5, fault determination is not executed.

Firstly, checked as step S6 are whether temperatures of the controller 12 and PM sensor 6 are beyond the dew point or not as well as whether the temperature of the exhaust gas G is within a proper range or not. This is because, in the condition of the temperatures not more than the dew point, the controller 12 and the PM sensor 6 may be broken as mentioned in the above; too high exhaust temperature may cause spontaneous combustion of the produced particulate matter, resulting in no deposition of the particulate matter on the PM sensor 6 irrespective of the particulate matter filter 5 being normal or not, and thus failing in proper fault determination. In a case it is determined not to satisfy these conditions ("N" in step S6), the fault determination of the particulate matter filter 5 is once given up. And the PM sensor 6 is regenerated again to redo fault determination of the particulate matter filter 5; alternatively, fault diagnosis is ended to await a next start of the engine (steps S19-S22 detailed hereinafter).

When it is determined to satisfy the above conditions in step S6 ("Y" in step S6), the procedure goes to step S7 where checked is whether the PM sensor 6 is in a state capable of properly measuring the deposition amount of the particulate matter, i.e., in an operating state capable of precisely outputting the output current 6a depending on the deposition amount of the particulate matter. Because, a value of electric resistance between the electrodes 11 is dependent on not only the deposition amount of the particulate matter but also various factors such as temperature so that, in some state of the PM sensor 6, the output current 6a may not be outputted properly depending on the deposition amount of the particulate matter. Whether the PM sensor 6 is in the state capable of properly measuring the deposition amount of the particulate matter or not is read from maps and functions preliminarily inputted in the controller 12, on the basis of the temperature of the exhaust gas G and other conditions.

When the PM sensor 6 is determined to be properly capable of measuring the deposition amount of the particulate matter in step S7 ("Y" in step S7), lapse time from the start of the monitoring in step S5 is added together with one count-up of the valid value counter (step S8). On the other hand, if the PM sensor 6 is determined not to be in the state capable of measuring the deposition amount of the particulate matter ("N" in step S7), only the lapse time is added (step S9).

Here, from the start of the monitoring, the virtual output value depending on the virtual deposition amount of the particulate matter in the PM sensor 6 is cumulated momentarily whereas, in the controller 12, estimated time from the start of the monitoring up to the reaching of the virtual output value to the predetermined determination threshold $\alpha$ is calculated on the basis of the virtual output value or a derivative value thereof. And, as step S10, a value of the time counter added in step S8 or S9 is compared with the estimated time up to the reaching of the virtual output value to the predetermined determination threshold $\alpha$. When the value of the time counter is determined not to reach the estimated time ("N" in step S10), the procedure returns to step S4 (FIG. 5) and steps S4-S8 or S4-S9 are executed and repeated until the value of the time counter reaches the estimated time.

When the value of the time counter is determined to reach the estimated time ("Y" in step S10), the procedure goes to step S11 where it is determined whether the value of the valid value counter counted in step S8 during the repeatable steps S4-S10 after step 3 reaches not less than the predetermined valid determination threshold. In other words, here it is determined during from the start of the monitoring up to step S11 by what degree in term of time the PM sensor 6 is determined to be in the state capable of precisely measuring the deposition amount of the particulate matter. If the value of the valid value counter is less than the valid determination threshold ("N" in step S11), the fault determination of the particulate matter filter 5 is once given up. And the PM sensor 6 is regenerated again to redo the fault determination of the particulate matter filter 5; alternatively, the fault determination is ended to await a next start of the engine (steps S19-S22 detailed hereinafter).

If in step S11 the value of the valid value counter is not less than the valid determination threshold ("Y" in step S11), the procedure geos to step S12. Now the stage is in step S12, the output value of the PM sensor 6 can be recognized to be reliable so that the virtual output value of the PM sensor 6 cumulated from the start of step S5 (the determination is executed when the virtual output value reaches the determination threshold α so that the virtual output value at this point of time is equal to the determination threshold α) is compared with the actual output current 6a from the PM sensor 6. If the actual output current 6a is not less than the virtual output value (determination threshold α) ("Y" in step S12), the determination number counter and the fault counter are respectively counted up by one (step S13) whereas if the output current 6a is less than the virtual output value (determination threshold α) ("N" in step S12), only the determination number counter is counted up by one (step S14).

Next, as step S15, it is determined whether the value of the determination number counter is not less than a predetermined diagnosis execution threshold. When the value of the determination number counter is less than the diagnosis execution threshold ("N" in step S15), the regeneration of the PM sensor 6 is requested again (step S22) and the procedure returns to step S2 (FIG. 5). Thus, steps S2-S15 are repeated until the value of the determination number counted in step S13 or S14 reaches the diagnosis execution threshold.

When the value of the above-mentioned determination number counter is determined to reach the diagnosis execution threshold in step S15 ("Y" in step S15), the procedure goes to step S16 (FIG. 7) where it is finally diagnosed whether the particulate matter filter 5 has fault or not. Here, the value of the determination number counter counted in step S13 or S14 in the repeated steps S2-S15 is compared with the value of the fault counter counted in step S13. If the value of the fault counter divided by the value of the determination number counter makes a value not less than a predetermined fault diagnosis threshold, then the particulate matter filter 5 is diagnosed as having fault. If the value of the fault counter divided by the value of the determination number counter makes a value less than the fault diagnosis threshold, then the particulate matter filter 5 is diagnosed as normal. That is, whether the particulate matter filter 5 has fault or not is diagnosed by a ratio of the number determined to have fault in a total number of the determinations.

If the particulate matter filter 5 is diagnosed as having fault ("Y" in step S16), the fault announcement signal 21a is inputted, as step 17, from the controller 12 to the alarm lamp 21 to switch on the lamp 21 (see FIG. 1) and announce the fault of the particulate matter filter 5 to the driver; thus, fault diagnosis of the particulate matter filter 5 is ended. When the particulate matter filter 5 is diagnosed as normal (from "N" in step S16 to step S18), the fault diagnosis of the particulate matter filter 5 is ended as it is.

Processing will be described in a case where, in step S6, it is determined not to satisfy the conditions for the fault determination of the particulate matter filter 5 ("N" in step S6 in FIG. 6) or where, in step S11, the value of the valid value counter is less than the valid determination threshold ("N" in step S11 in FIG. 6). These are cases where no determination is possible or no output value of the PM sensor 6 is reliable so that the fault determination of the particulate matter filter 5 is once given up as mentioned in the above. Specifically, started is checking a regeneration number of the PM sensor 6 after the start of the engine (step S19). An upper limit of the regeneration number (a regeneration upper limit) in one driving is set in the embodiment since the detection portion 7 of the PM sensor 6 with the ceramic foundation 10 and the metallic electrodes 11 is limitative in heat resistance and tends to be deteriorated in precision or broken in a great number of repeated regenerations. If in step S20 a number of inputting the regeneration signal 6b to the PM sensor 6 after the start of the engine 1 reaches the regeneration upper limit ("Y" in step S20), the fault diagnosis of the particulate matter filter 5 is given up to end the fault diagnosis and await a next driving (step S21). When the number of inputting the regeneration signal 6b is still lower than the regeneration upper limit ("N" in step S20), the procedure goes to step S22 where regeneration of the PM sensor 6 is requested to execute the fault determination of the particulate matter filter 5 again (steps S2 ff. in FIG. 5).

Thus, in this manner, the fault diagnosis is executed by employing only the output value in a case where the PM sensor 6 is in the state capable of outputting the output value depending on the deposition amount of the particulate matter, which can further enhance precision of the fault diagnosis of the particulate matter filter 5.

Thus, according to the above-mentioned embodiment, fault in a particulate matter filter can be precisely and favorably determined.

It is to be understood that a method and a device for making fault diagnosis according to the invention is not limited to the above embodiment and that various changes and modifications may be made without departing from the scope of the invention.

REFERENCE SIGNS LIST 3 exhaust pipe
5 particulate matter filter
6 PM sensor
7 detection portion
12 controller

The invention claimed is:

1. A method for making fault diagnosis of a particulate matter filter, the method comprising:
arranging a PM sensor downstream of the particulate matter filter incorporated in an exhaust pipe, said PM sensor having a detection portion on which particulate matter is deposited to output a deposition amount of said particulate matter,
setting an assumption condition for making assumption that said particulate matter filter is in a reference state having a predetermined particulate matter capturing capability,
calculating a virtual output value in said PM sensor depending on a virtual deposition amount of the particulate matter under said assumption condition, and determining said particulate matter filter to have fault when, upon reaching of said virtual output value to a saturation output value of said PM sensor which is a maximum output value of said PM sensor, an output of said PM sensor is not less than said saturation output value.

2. The method for making fault diagnosis of the particulate matter filter as claimed in claim 1, wherein the fault diagnosis is executed by employing only the output value in a case where said PM sensor is in a state capable of outputting the output value depending on the deposition amount of the particulate matter.

3. A device for making fault diagnosis of a particulate matter filter comprising:
   a particulate matter filter incorporated in an exhaust pipe,
   a PM sensor arranged downstream of said particulate matter filter and having a detection portion on which particulate matter is deposited to detect the particulate matter in exhaust gas, and
   a controller with an assumption condition being set for making assumption that said particulate matter filter is in a reference state having a predetermined particulate matter capturing capability, wherein said controller calculates under said assumption condition a virtual output value in said PM sensor depending on a virtual deposition amount of the particulate matter and determines said particulate matter filter to have fault when, upon reaching of said virtual output value to a saturation output value of said PM sensor which is a maximum output value of said PM sensor, an output of said PM sensor is not less than said saturation output value.

4. The device for making fault diagnosis of the particulate matter filter as claimed in claim 3, wherein said fault diagnosis is adapted to be executed by employing only the output value in a case where said PM sensor is in a state capable of outputting the output value depending on the deposition amount of the particulate matter.

* * * * *